United States Patent [19]

Sprunt et al.

[11] Patent Number: 4,631,963

[45] Date of Patent: *Dec. 30, 1986

[54] METHOD FOR MEASURING ACOUSTIC ENERGY ANISOTROPY THROUGH CORE SAMPLES

[75] Inventors: Eve S. Sprunt, Farmers Branch; Larry D. Smallwood, Duncanville, both of Tex.

[73] Assignee: Mobil Oil Corporation, New York, N.Y.

[*] Notice: The portion of the term of this patent subsequent to Dec. 30, 2003 has been disclaimed.

[21] Appl. No.: 715,796

[22] Filed: Mar. 25, 1985

[51] Int. Cl.⁴ .................................................. G01N 29/00
[52] U.S. Cl. .................................... 73/594; 73/571; 73/597; 73/599; 367/13
[58] Field of Search ................. 73/571, 594, 599, 618, 73/632, 597; 367/13

[56] References Cited

U.S. PATENT DOCUMENTS 3,537,541 11/1970 Desai et al. .......................... 73/594
4,380,930 4/1983 Podhrasky et al. .................. 73/594

Primary Examiner—Howard A. Birmiel
Attorney, Agent, or Firm—Alexander J. McKillop; Michael G. Gilman; George W. Hager, Jr.

[57] ABSTRACT

Acoustic energy anisotropy is measured in a core sample from a subterranean formation. The core sample is shaped by having its outer surface cut to provide a plurality of pairs of parallel, planar outer surfaces about the length of the core sample. A pair of planar transducers are successively placed in contact with each of the pairs of parallel, planar outer surfaces, one of the transducers being a transmitting transducer and the other being a receiving transducer. Compressional or shear acoustic energy is transmitted through the core sample in the azimuthal directions that are perpendicular to each of the pairs of parallel, planar outer surfaces of the core sample. Any differences in travel time, attenuation, waveform or other acoustic properties for the acoustic energy transmissions in the plurality of differing azimuthal directions are a measure of the compressional or shear acoustic energy anisotropy of the subsurface formation.

7 Claims, 3 Drawing Figures

METHOD FOR MEASURING ACOUSTIC ENERGY ANISOTROPY THROUGH CORE SAMPLES

BACKGROUND OF THE INVENTION

In sedimentary rocks, large vertical changes in properties occur as the result of changes in depositional conditions. Horizontal (or lateral) changes within a formation are known to occur, but these are generally much smaller. However, such changes may be of great importance in petroelum exploration and production. This variation of a property or properties with direction is termed "anisotropy". For example, horizontal anisotropy of elastic properties may affect the interpretation of seismic prospecting data. Petroleum production permeability anisotropy, caused by preferential arrangement of pores and/or fractures, is often an important factor in both primary and enhanced recovery. Stress anisotropy is important in petroleum well stimulation by hydraulic fracturing because the azimuth of induced fractures is generally parallel to the maximum horizontal stress direction. In many cases, the directions of natural and induced fractures are coincident.

SUMMARY OF THE INVENTION

The present invention is directed to a method for measuring changes in acoustic velocity, attenuation, waveform or other acoustic properties which indicate the presence of lateral mechanical anisotropy in a core sample, taken from a subterranean formation, due to fractures, stress and other factors.

After the core sample is taken from a subterranean formation, it is shaped by having its outer surface cut or planed to provide a plurality of pairs of parallel, flat or planar surfaces about the core sample. A pair of planar acoustic transducers are successively placed in contact with each pair of planar outer surfaces, one of the transducers being a transmitting transducer and the other being a receiving transducer. Compressional or shear acoustic energy is transmitted through the core sample from the transmitting transducer to the receiving transducer in the azimuthal direction that is perpendicular to the pair of parallel, planar outer surfaces. Thereafter, such acoustic energy is transmitted through each of the plurality of differing azimuthal directions that are perpendicular to the plurality of parallel, planar surfaces of the core sample. The measured acoustic properties are compared to identify the azimuthal direction of any acoustic energy anisotropy through the core sample. The acoustic properties measurements may be carried out for opposite paths of travel of the acoustic energy in each of the azimuthal directions through the core sample.

In one aspect of the invention, the pairs of parallel, planar outer surfaces may coexist, and the acoustic properties measurements can be made sequentially for each of such pairs of surfaces. In an alternate aspect, the pairs of parallel, planar outer surfaces do not coexist, and the acoustic properties measurements will be made for each of such pairs of surfaces prior to the sequential formation of the next such pair of surfaces.

In still another aspect, the horizontal acoustic energy anisotropy of the subterranean formation from which the core sample was taken is obtained by shaping the core sample such that the perpendiculars to the plurality of pairs of parallel, planar outer surfaces correspond in orientation to the horizontal orientation of the core sample prior to being taken from the subterranean formation.

DESCRIPTION OF THE PREFERRED EMBODIMENT

Figure 1:
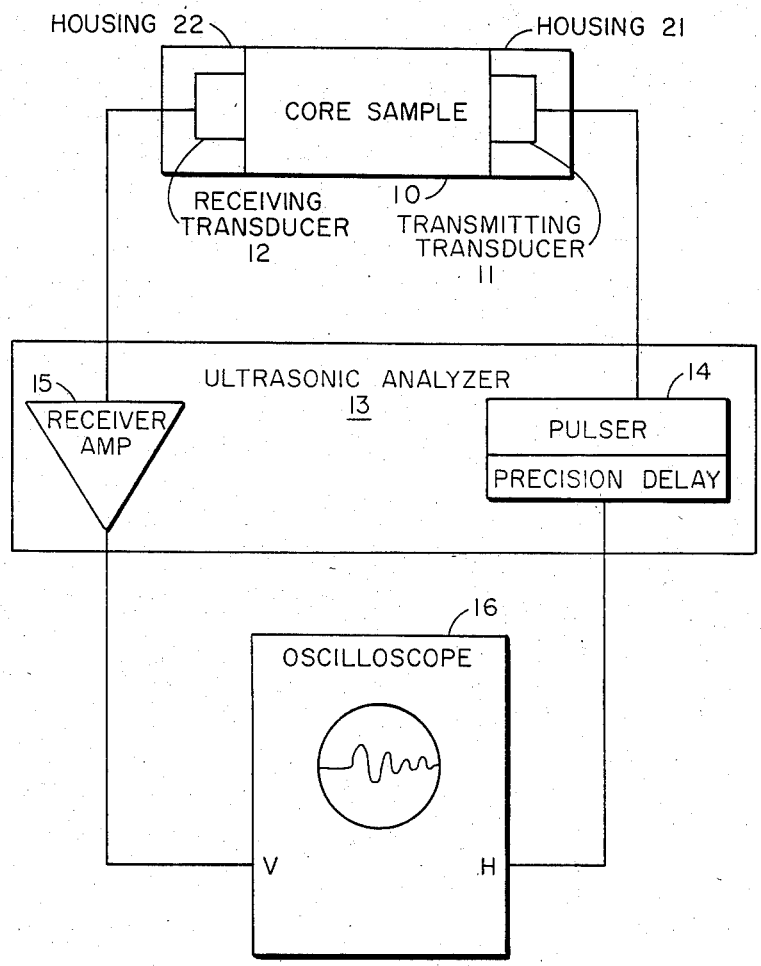
FIG. 1 illustrates a system for measuring acoustic velocity and recording waveforms of core samples from subterranean formations.

Referring now to FIG. 1, the core sample 10 from a subterranean formation to be examined in accordance with the present invention is mounted between a transmitting transducer 11 and its housing 21 and a receiving transducer 12 and its housing 22. These transducers are acoustic energy devices, such as piezoelectric or magnetostrictive crystals, designed to transmit and receive acoustic signals. Generation of the acoustic signal is carried out by the analyzer 13 including a pulser section 14 and a receiver section 15. The pulser section 14 produces an electrical pulse to excite the transmitting transducer 11, causing it to emit an ultrasonic pulse. This pulse travels through the material of core sample 10 and is converted by the receiving transducer 12 into an electrical signal which is applied to and conditioned by the receiver section 15 of the analyzer 13. This technique is called the "through transmission" technique as the pulse is transmitted by one transducer and received by another. An alternate embodiment might employ the "pulse-echo" technique whereby the pulse travels from the transducer through the material until it is reflected from an interface, such as the other end of the core sample. The reflected pulse may be received by the same transducer and converted into an electrical signal.

In either embodiment, the electrical signal, after being conditioned by the receiver section 15 of the analyzer 13, may be displayed on an oscilloscope 16 for visual interpretation and travel time calculation. The signal may also be recorded by other suitable devices, such as a Tektronix 7912AD model digital waveform recorder 17 or a strip chart recorder 19, for analysis.

The analyzer 13 may be a Panametrics, Inc. Model 5055PR, which combines a pulser/receiver in a single unit. The oscilloscope 16 may be a Hewlett-Packard 1743A model, which provides a dual time base with suitable time and amplitude expansion for an accurate selection of the acoustic time break.

Figure 2:
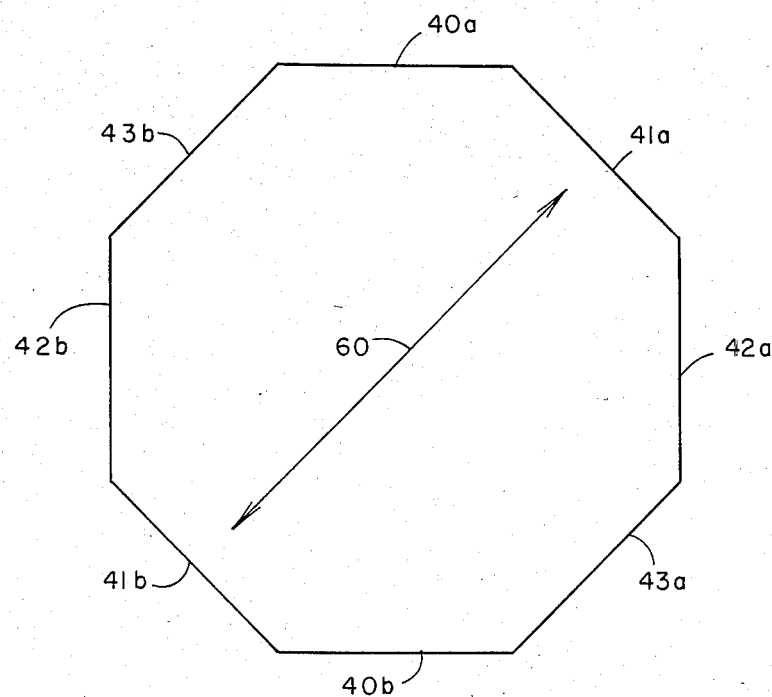
FIGS. 2 and 3 are top views of a core sample showing alternate emobidments of the shaping of the core sample for the carrying out of the method of the present invention.

Compressional or shear acoustic travel time, attenuation and waveforms through the core sample 10 are obtained by shaping the core sample to provide a plurality of pairs of parallel, planar outer surfaces along the length of the core sample. The core sample does not have to be a right circular cylinder or a regular prism shape. Only the two surfaces of each pair of surfaces need to be planar and parallel. Such a shaping of the core sample may be better understood by referring to FIG. 2, which is a top view of a core sample which has been shaped, for example, in the form of a polygon, and, more specifically, an octagon. Four pairs of parallel, planar outer surfaces have been formed 40a and 40b; 41a and 41b; 42a and 42b; and 43a and 43b. Acoustic wave energy is transmitted and received between each of the pairs of parallel, planar surfaces. For example, the core sample is mounted in the housings 21 and 22, as shown in FIG. 1, with the transmitting transducer on surface 40a and the receiving transducer on surface 40b. The measurements of acoustic properties through the core sample from surface 40a to surface 40b are representative of the acoustic properties through the core sample in the azimuthal direction perpendicular to such surfaces. The core sample is then reoriented in the housings 21 and 22 to successively measure acoustic properties between the surfaces 41a and 41b; 42a and 42b; and 43a and 43b. In this manner, the azimuthal direction of the acoustic energy wave through the core sample is successively changed so as to effect differing transmission paths. The acoustic energy properties among such differing transmission paths are compared and any changes in the observed travel time, attenuation, waveform or other acoustic properties are indications of acoustic energy anisotropy of the core sample. These acoustic properties measurements may be carried out in opposite azimuthal directions between each of the pairs of surfaces as indicated by the double headed arrow 60 in FIG. 2, for example.

Figure 3:
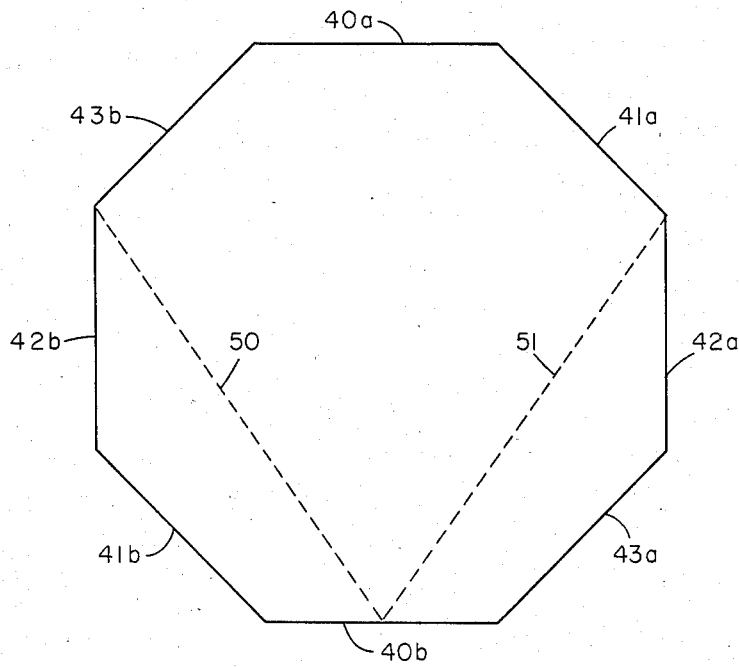

FIG. 3 illustrates an alternate embodiment for the shaping of the core sample for the carrying out of the acoustic energy measurements of the present invention. In this alternate embodiment, all the desired pairs of parallel, planar outer surfaces do not have to coexist since select pairs of surfaces may be formed only upon the destruction of other pairs of surfaces. For example, surfaces 50 and 51, as shown by dashed lines in FIG. 3, could be formed in parallel with surfaces 43b and 41a, respectively, by the destruction of surfaces 42a, 43a, 40b, 41b and 42b. With the embodiment of FIG. 1, all acoustic energy measurements can be made after completion of the core shaping, whereas with the embodiment of FIG. 2, certain of the acoustic energy measurements, such as between surfaces 42a and 42b, must be made before such pair of surfaces are destroyed to form the pair of parallel, planar surfaces 50 and 51 between which an acoustic energy measurement is also desirable.

It is a specific feature of the present invention to measure the horizontal acoustic energy anisotropy of the subterranean formation from which the core sample was taken. This measurement is carried out by shaping the core sample such that the perpendiculars to the plurality of pairs of parallel, planar surfaces correspond in orientation to the horizontal orientation of the core sample prior to being taken from the subterranean formation.

In carrying out such acoustic properties measurements, the transducers 11 and 12 are held rigid and pressed against the selected pair of surfaces of the core sample. To ensure good contact, a simple press is utilized to provide a fixed pressure. One such press that has been successfully employed is described and illustrated in detail in U.S. Pat. No. 4,380,930 to Podhrasky and Sprunt, such U.S. patent being specifically incorporated herein by reference. Transducers 11 and 12 may be any suitable commercial, planar transducers for the generation of symmetrical (compressional) or asymmetrical (shear) acoustic energy waves, such as Panametrics Models V102 and V152, respectively.

While the foregoing preferred embodiments of the invention have been described and illustrated, numerous modifications or alterations may be made without departing from the spirit and scope of the invention as set forth in the appended claims.

We claim:

1. A method for measuring acoustic energy anisotropy of a core sample from a subterranean formation, comprising the steps of:
    (a) shaping said core sample to provide a plurality of pairs of parallel, planar outer surfaces about the length of said core sample,
    (b) measuring acoustic travel time, attenuation, waveform or other acoustic properties through said core sample in each of the azimuthal directions through said core sample which are perpendicular to each of said pairs of parallel, planar outer surfaces, and
    (c) comparing each of said measured acoustic properties to identify the azimuthal direction of any acoustic energy anisotropy through said core sample.

2. The method of claim 1 wherein each of said acoustic properties measurements is carried out for opposite paths of travel of acoustic energy for each of said azimuthal directions through said core sample.

3. The method of claim 1 wherein the shaping of said core sample comprises the sequential formation of each of said pairs of parallel planar outer surfaces.

4. The method of claim 3 wherein each of said pairs of parallel planar outer surfaces coexist and said acoustic properties measurements are made sequentially for each of said pairs of parallel, planar outer surfaces.

5. The method of claim 3 wherein acoustic properties measurement are made for each pair of said parallel planar outer surfaces prior to the sequential formation of the next pair of said parallel, planar outer surfaces.

6. The method of claim 3 wherein:
    (a) the sequential formation of at least one of said pairs of parallel, planar outer surfaces destroys at least one other of said pairs of parallel, planar outer surfaces and acoustic properties measurements are made for each pair of said parallel, planar outer surfaces prior to the sequential formation of the next pair of said parallel, planar outer surfaces.

7. The method of claim 1 wherein the shaping of said core sample is such that the perpendiculars to said plurality of pairs of parallel, planar outer surfaces correspond in orientation to the horizontal orientation of said core sample prior to being taken from the subterranean formation.

* * * * *